United States Patent
Kamentsky

[11] Patent Number: 5,633,945
[45] Date of Patent: May 27, 1997

[54] ACCURACY IN CELL MITOSIS ANALYSIS

[75] Inventor: Lee D. Kamentsky, Arlington, Mass.

[73] Assignee: CompuCyte Corporation, Cambridge, Mass.

[21] Appl. No.: 318,233

[22] Filed: Oct. 5, 1994

[51] Int. Cl.$^6$ .................................................. G06K 9/36
[52] U.S. Cl. ........................ 382/129; 382/279; 435/808
[58] Field of Search .................................. 382/128, 129, 382/133, 134, 279; 364/413.08, 413.1; 435/61, 808

[56] References Cited

U.S. PATENT DOCUMENTS 5,107,422  4/1992  Kamentsky et al. .................... 382/133
5,202,230  4/1993  Kamentsky ................................ 435/6

OTHER PUBLICATIONS

Van Dilla et al., "High Speed cell analysis & sorting with flow systems . . . " IEEE transactions on Nuclear Science vol. 21, No. 1 pp. 714–720 Feb. 1974.

Rigaut et al., "The 'Corpuscle' Stereological problem–re-evaluation using slab Frasment Volumes and application to the correction of DNA histograms from selections of spherical nuclei", Journal of Microscopy, vol. 156, pt. 3 pp. 371–382, Dec. 1989.

Schultz et al., "Identification of the Flow Cytometry Systems for DNA Histogram Analysis purposes," IFAC Identification & System Parameter Estimations, vol. 1, pp. 1131–1136, 1985.

*Primary Examiner*—Joseph Mancuso
*Assistant Examiner*—Larry J. Prikockis
*Attorney, Agent, or Firm*—Graham & James LLP

[57] ABSTRACT

Cell samples, stained with a fluorescent dye, taken up by DNA in the individual cells, are scanned with a cytometer, which measures the integrated value of fluorescent light/cell. The integrated values of all of the cells are compiled to create an histogram of cell counts versus integrated fluorescent light, representing a cell population of (a) cells having a complement of DNA, but not in the process of division ($G_0$ phase), (b) cells having two full compliments of DNA, but which have not actually divided into two cells ($G_2$ phase) and (c) cells which are in the process of replicating their DNA (S, separation phase). The percentages of cells in each of the phases, represented in the histogram as separated peaks of sizes proportional to the $G_0$ and $G_2$ populations, and separation S phase population, aids in the prognosis of a patient's cancer development. More serious malignancy is indicated by increased S and $G_2$ phase populations. Errors, e.g., resulting from statistical errors, focusing problems, inaccurate measurement of background, etc., in the integrated values and compilation of cells in the histogram, affect the accuracy and prognostic value of the peaks and separation phase, and are corrected by a method, wherein the convolution of error function with the signal function (representing the number of cells, as determined by the florescence measurements, with a DNA content of a specified value), is modeled and the error function removed, by deconvolution, from the $G_0$ and $G_2$ peaks and the S phase.

9 Claims, 8 Drawing Sheets

ACCURACY IN CELL MITOSIS ANALYSIS

FIELD OF THE INVENTION

This invention relates to cytometric measurement of DNA content of cells for the determination of cell mitosis, in the prognosis of cancer stages and development.

BACKGROUND OF THE INVENTION

Cells grow through mitosis and the individual cells can be identified or classified, through their progression by mitosis, with a determination of the amount of DNA in the cell. The cells are generally categorized into three classes or "populations":

a) normal cells, or cells which are not in the process of division ($G_0$ phase) which normally make up the bulk of the population. These cells have a base complement of DNA;

b) cells which are in the process of replicating their DNA (S phase) with varying fractional amounts of additional DNA above the base level; and c) cells which have two full complements of DNA but which have not actually divided into two cells ($G_2$ phase).

Physicians and oncologists find that a percentage determination of the cells in each phase is useful in a prognosis of a patient's cancer development, since efficacy of different treatments is dependent on the stage of cancer development. A cell population with more cells in the S and $G_2$ phases is indicative of a faster rate of cell mitosis and a probably more serious malignant state.

A dye absorption property of DNA has been utilized, in devices and developed procedures, to discriminate between the various cell types or classes. This permits calculation of the percentages of cells, contained in each of the aforementioned populations, in large scale cell analysis.

In a common procedure, fluorescent dyes are used to stain the cells, with the dye being taken up only by the DNA in the cells. Scanning of the cells with a laser excites the dye to fluoresce, with the amount of light thus obtained from each cell being roughly proportional to the DNA content of the cell.

A cytometer or flow cytometer (using a stationary slide sample of cells and a cell-aligned flowing cell sample, respectively) is used to effect such fluorescing, light measurement, and proportional determination of percentage cells with different DNA content. Characteristics of flow cytometers are described, for example in *Characteristics of Flow Cytometers* by Harald B. Steen in *Flow Cytometry and Sorting*, pp 11–25 (Wiley-Liss, Inc. 1990, 2nd ed.), the disclosure of which is incorporated herein by reference thereto. A microscope based, stationary sample cytometer is disclosed in U.S. Pat. Nos. 5,072,382 and 5,107,422, issued to Louis A. Kamentsky, the disclosure of which is also incorporated herein by reference thereto.

Typically, several thousand cells are scanned in a cytometric sample and their relative DNA contents are recorded in the form of an histogram of cell DNA content, which is utilized in cancer prognosis. The accuracy of the relative percentages is important for a better understanding of the cancer development stage and with respect to decisions regarding appropriate treatment.

In the past, the distributions of cell populations of the histograms have been analyzed using standard statistical methods. With such methods, the errors in each of the $G_0$ and $G_2$ phases are modelled as Gaussian, with a constant coefficient of variation. The S phase has been modeled in a number of different ways: as a first or second degree polynomial, or as a series of trapezoids. A least squares fit is applied to the model to arrive at the actual population counts of the three phases (as described in "Data Processing", by Phillip N. Dean, *Flow Cytometry and Sorting*, second ed., pages 415–444 (Wiley-Liss, Inc. 1990)).

However, the values obtained by this statistical modeling have been discovered to conflict with or deviate significantly from results which would be expected to be obtained by an actual visual inspection of the cell data of distribution in the same sample. In particular, it has been discovered that the S phase model, as determined by these prior art methods, is often overestimated. This limits the value of the histograms, so obtained, as a diagnostic tool.

It is therefore an object of the present invention to provide a method for the accurate determination of relative cell populations based on their DNA content.

It is a further object of the present invention to provide such method for accurate determination of relative cell populations based on their DNA content, by means of large scale cytometric cell scanning.

These and other objects, features and advantages of the present invention will become more evident from the following discussion and drawings in which:

SUMMARY OF THE INVENTION

Generally the present invention comprises a method for the determination, with greater accuracy, of relative percentage populations of cells in biological samples, such as blood cell samples, having varying complements of DNA, ranging from a baseline complement of DNA, in normal cells, to cells having two full complements of DNA, prior to splitting into two cells.

The method of the present invention comprises the steps of:

a) staining a testing sample of cells with a fluorescent dye which is taken up only by the DNA within the individual cells;

b) using fluorescing means, such as a laser, to excite the taken up dye within the cells, whereby light is emitted from the individual cells, in substantial proportion to the DNA content therewithin;

c) measuring the emitted light relative to the number of cells within the testing sample and relating the measured light to DNA content within said cells;

d) preparing an histogram of relative cell populations of said testing sample having different DNA contents;

e) modeling the relation of the number of cells, as determined by the florescence measurements, with a DNA content of a specified value (signal function), relative to an error function inherent in said measurements; for each of the cell populations with differing DNA contents; and d) deconvoluting the error function from the signal function with deconvolution means and correcting the histogram at each of the differing DNA contents populations to reflect substantially only the signal function.

DETAILED DESCRIPTION OF THE INVENTION

In the prior art, analytic histograms have been prepared and corrected for errors with the assumption that the signal (the histogram of actual DNA content) is convoluted by an error function as represented by:

$$H(x) = \int S(x')E(x-x')dx'$$

With x representing the amount of DNA in the cell and the signal function S representing the number of cells with a DNA value of a particular x.

The prior art statistical method postulates a function $S(x')$, with variable coefficients and computes these coefficients so as to minimize the difference between the integral and the observed histogram $H(x)$, with the assumption that the coefficients are optimally adjusted by finding the minimum. However, a fallacy in such assumption exists in that those elements of $S(x')$ that have more coefficients (e.g., the S phase in a second order polynomial model have three coefficients will tend to have disproportionately more cells assigned to them than those elements that have less coefficients (e.g., $G_0$ which has one coefficient). It is thus possible that with such prior art analysis, at least half of the cells of the $G_0$ and $G_2$ phases are assigned to the S phase.

In accordance with the present invention, such incorrect assignment of cell type, is avoided. The signal function, defined as representing the number of cells with a DNA of a particular value, is modeled with its interaction with an error function at that value (the error function, for example, resulting from statistical errors, focusing problems, inaccurate measurement of background, etc.) in a convolution of the signal function S by the error function E, as described and represented as above.

In accordance with the method of the present invention, with an inverse fast Fourier transform, a relation between the histogram $H(x)$, cell distribution $S(x)$ and error function $E(\Delta x)$ is represented as:

$$S(x) = \mathfrak{I}^{-1}\left(\frac{\mathfrak{I}(H(x))}{\mathfrak{I}(E(\Delta x))}\right)$$

Thus, the cell distribution $S(x)$ is derived from the histogram $H(x)$ and the error function ($E\Delta x$), by taking the inverse fast Fourier transform of the quantity, the fast Fourier transform of the histogram divided by the fast Fourier transform of the error function.

Though the error function has a dependence on x as well as $\Delta x$ it is sufficiently small enough such that the error function does not deviate significantly from a function, solely dependent on $\Delta x$ over the measured distributions of the $G_0$ and $G_2$ peaks. Accordingly, the transforms are performed in a piecewise analysis or deconvolution, using a standard deviation equal to the constant coefficient of variation (COV) times the DNA value at $G_0$. The $G_0$ peak that becomes apparent is subtracted out of the histogram. Similarly, the transforms are performed at $G_2$ and the peak is subtracted out at that location.

The deconvolution obtained in this manner most commonly assumes a Gaussian error function, with a standard deviation being that of the leading edge of the $G_0$ peak. Deconvolution, in accordance with the present invention is equally applicable to any error function convoluted with a signal function and, is accordingly not limited to only a Gaussian error function. Thus, for example, measurement of the inherent machine error function may be made by using a sample of cells which are all in the $G_0$ state. The histogram of integrated fluorescence would be the machine's error function. This error function is then substituted for the Gaussian during deconvolution and reconvolution.

With respect to a deconvolution involving a Gaussian error function, it should be understood that the error function is not a perfect Gaussian and accordingly, the $G_0$ peak so derived is not a perfect delta function. The histogram may therefore exhibit "ringing" (negative deviation of the peak) due to a COV estimate which is too high. Accordingly, it is heuristically assumed that the $G_0$ portion of the deconvoluted histogram extends 8% to either side of the $G_0$ peak, with the percentage being invariant with respect to the COV in the deconvoluted domain. The heuristic creates two histograms: (a) a histogram of the cells in the $G_0$ phase in the deconvoluted domain ($G_0$ Phase(x)), and (b) a histogram of the cells that are not in the $G_0$ phase in the deconvoluted domain (~$G_0$Phase(x)). The ~$G_0$Phase(x) is transformed back into the undeconvoluted domain as follows:

$$H'(x) = \mathfrak{I}^{-1}(\mathfrak{I}(\sim(G_0\text{Phase}(x))*\mathfrak{I}(E(\Delta x)))$$

A similar operation is applied to determine the $G_2$ phase:

$$S'(x) = \mathfrak{I}^{-1}\left(\frac{\mathfrak{I}(H'(x))}{\mathfrak{I}(E'(\Delta x))}\right)$$

where with microscope based cytometers, $E'(\Delta x)$ is a Gaussian whose standard deviation is twice that of $E(\Delta x)$ since the $G_2$ population has twice the DNA as the $G_0$ population. Accordingly, the constant COV is assumed to be twice that of the $G_0$ population (with flow cytometers, having a non-linearity of measurement, the measured $G_2$ fluorescence is about 195% of the $G_0$ and this percentage difference is used with flow cytometer measurements). The same heuristic percentage is utilized as in the $G_0$ phase in order to find the cell counts in the $G_2$ and S populations.

The above method is also applicable to histograms of aneuploid populations (populations of cells in which some of the cells have incorrectly manufactured multiple copies of some of their DNA) in order to obtain accurate cell counts of aneuploid populations. The aneuploid peak however rides on top of the S phase for non-aneuploid cells. The S phase is subtracted from the aneuploid peak in order to obtain the correct cell count for the aneuploid peak.

DETAILED DESCRIPTION OF THE DRAWINGS AND THE PREFERRED EMBODIMENT

Figure 1A:
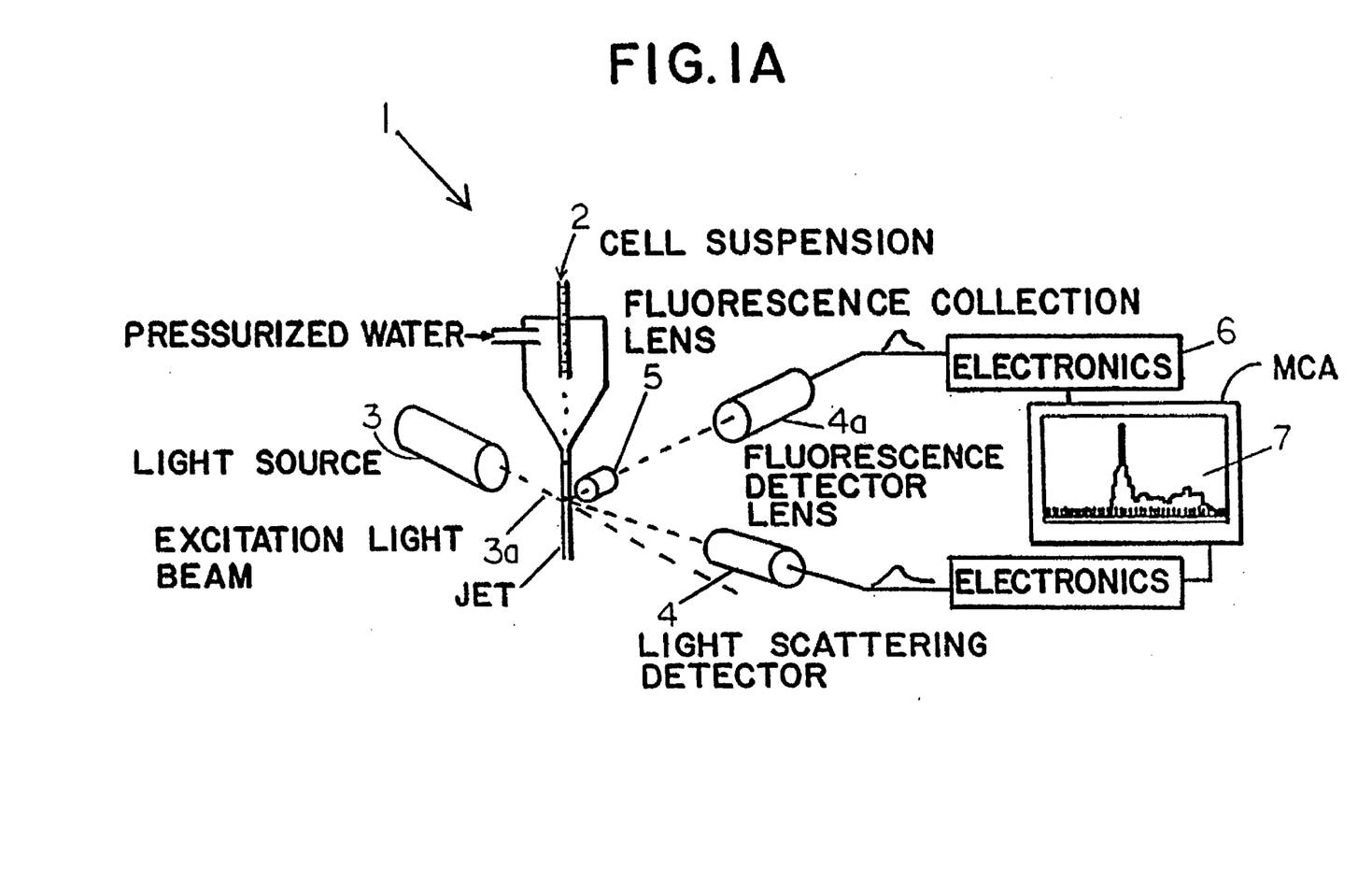
FIGS. 1a and 1b are schematic depictions of a flow cytometer and a microscope based cytometer respectively.

In a general overview of flow cytometer operation, and with specific reference to the aforementioned prior art (*Characteristics of Flow Cytometers*), FIG. 1a (FIG. 1 therein) shows a cytometer 1 with a flowing cell suspension 2 passing between a light source 3 excitation beam 3a, a light scattering detector 4, and a fluorescing collection lens 5. Light scattering detector and fluorescence detector 4a, collect respective detected outputs of fluorescence and light scattering, with appropriate electronics 6, converting the detected data into a histogram 7.

Figure 1B:
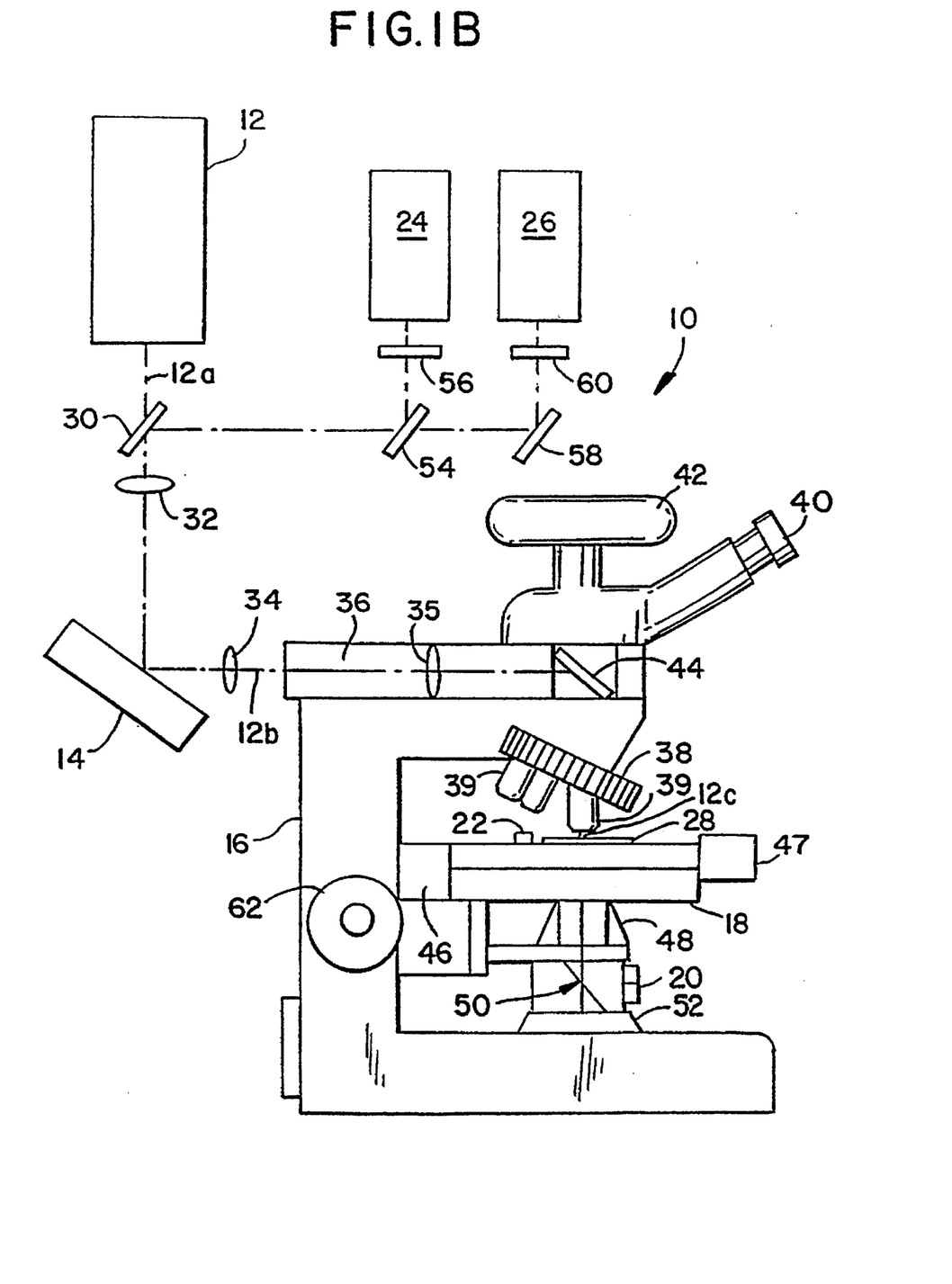

In a similar general overview of a microscope based cytometer, and with reference to the aforementioned U.S. patents, FIG. 1b (FIG. 1 therein) a microscope 16 with a movable stage is used to scan a slide 28 have a cell specimen thereon. The specimen is illuminated and fluoresced by light source 12, with sensors 20 and 22 sensing light scattering and sensors 24 and 26 sensing fluorescing whereby a histogram is created from the detected light.

Figure 2:
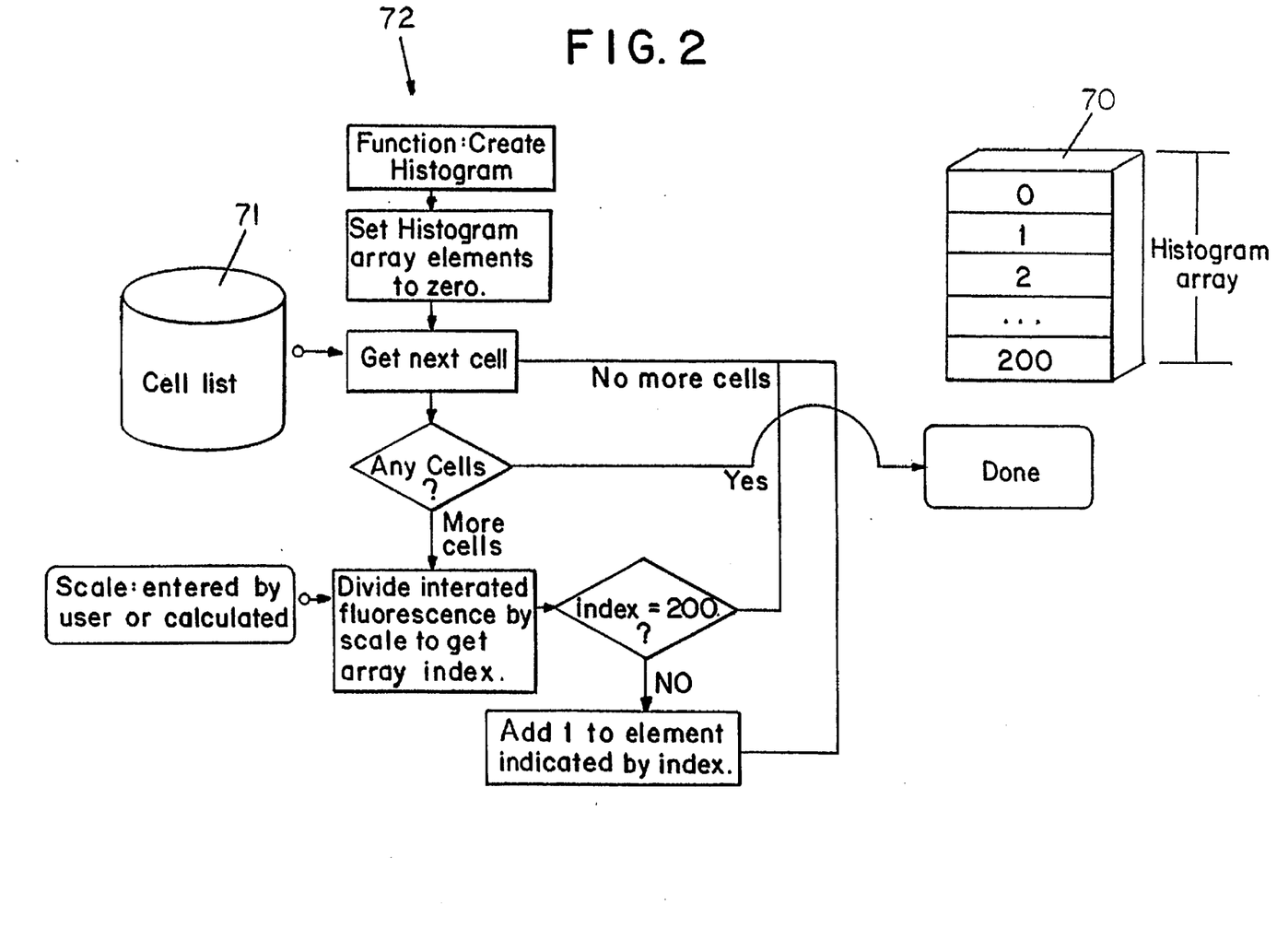
FIG. 2 is a flow chart and description of the creation of a typical histogram from cytometric measurements and analysis.

In FIG. 2, a histogram array 70 is created by the analysis of cells, as shown in the flow chart 72, based on the integrated fluorescence of the cells, as obtained from a cytometer such as in FIGS. 1a or 1b. Each element of the cell list 71 contains a record of the cell's integrated fluorescence. An histogram array is created in memory and it is composed of 200 channels or array elements. The histogram elements are initialized to zero. Channel N of the histogram will contain the number of cells in the cell list whose integrated fluorescence is between Scale*N and Scale*(N+1). A next cell is selected from the cell list until there are no more cells in the list. The histogram contains the counts of cells in its channels.

The integrated fluorescence is divided by the scale, thereby yielding the index 0 TO 199 of the channel to increment, or it yields an index >=200. If the index is less than 200, one is added to the count in the corresponding channel. This is repeated until there are no more cells.

Figure 3:
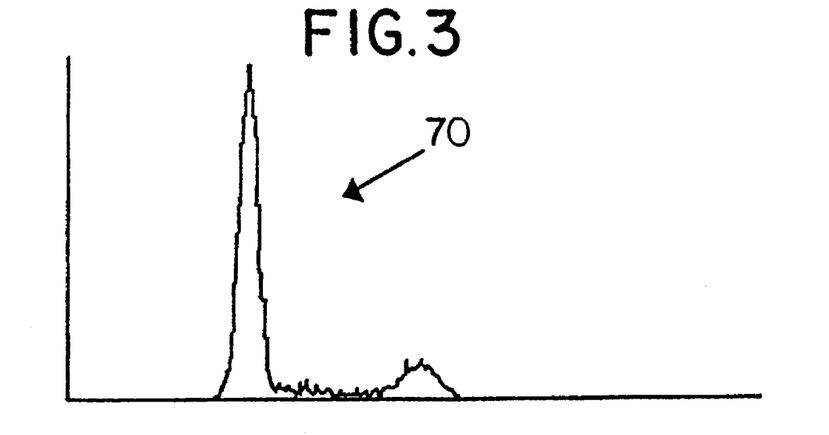
FIG. 3 is a typical initial histogram with $G_0$ and $G_2$ peaks and S region.
Figure 4:
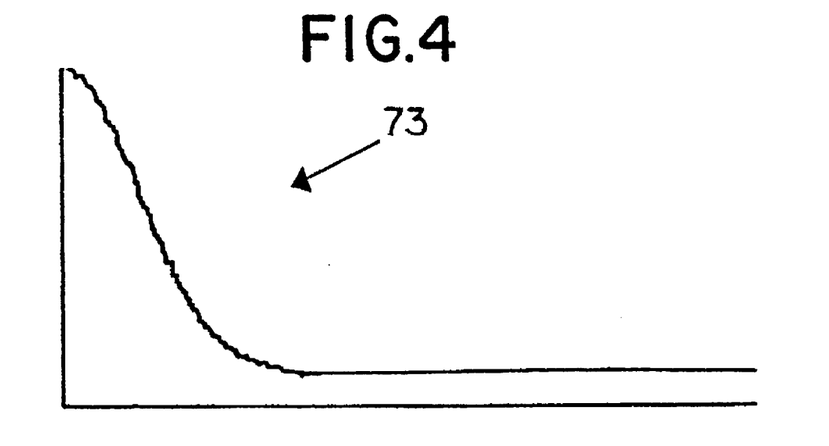
FIGS. 4–13 depict the stepwise deconvoluting and reconvoluting of histograms with Gaussian error function for accurate determination of $G_0$ and $G_2$ peaks and S region.
Figure 5:
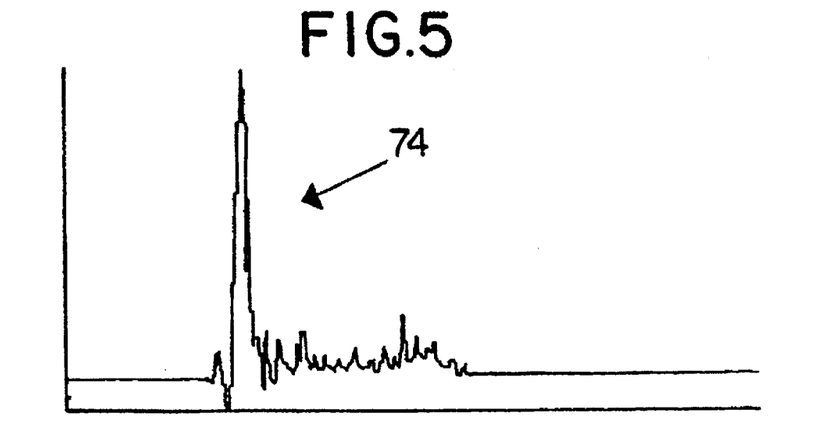
Figure 6:
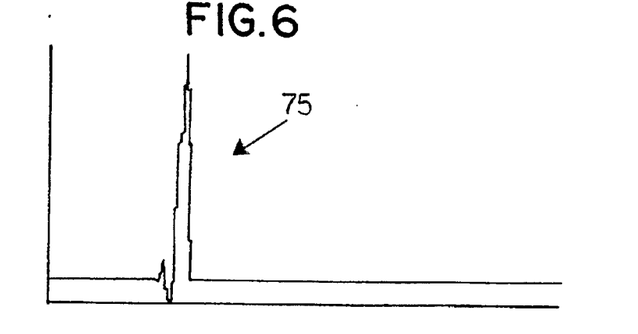
Figure 7:
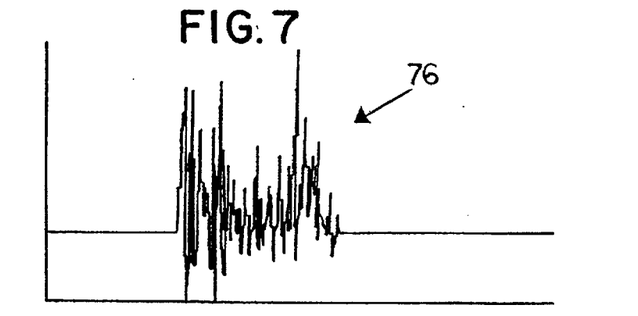
Figure 8:
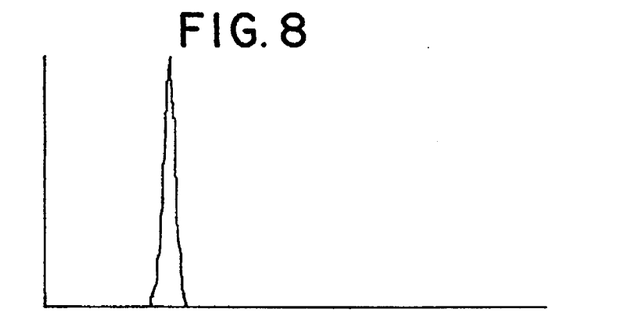
Figure 9:
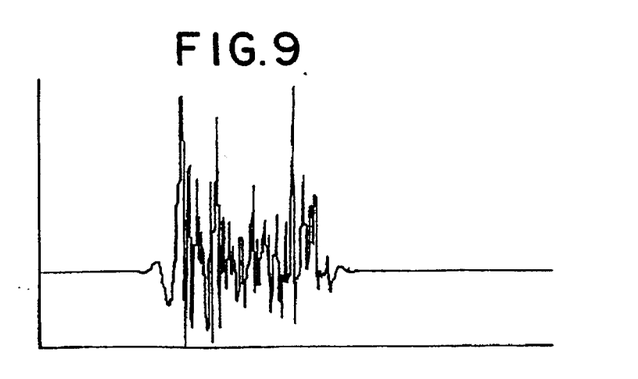
Figure 10:
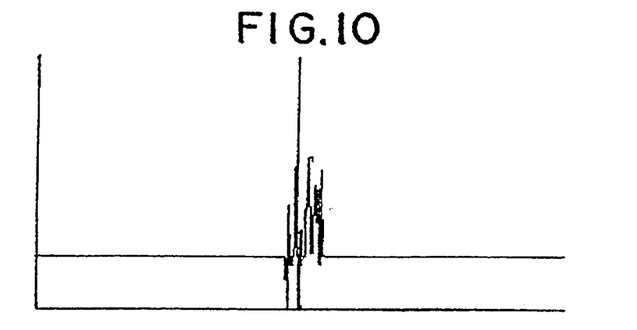
Figure 11:
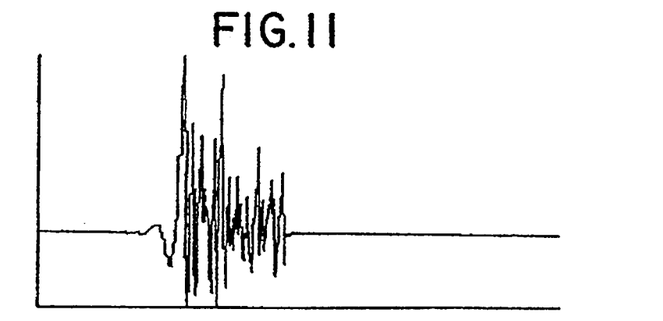
Figure 12:
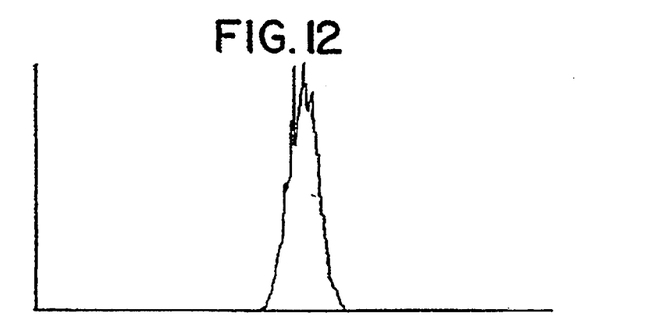

With reference to FIGS. 3–13, of illustrative histograms of various elements, the following steps are involved in separating a histogram of total DNA into its $G_0$, S and $G_2$ components:

1. Starting with the histogram 70 in FIG. 3, which is the initial histogram created by the original process, determining that the channel A, containing the most cells is the peak channel;

2. determining the constant coefficient of variation (COV) from the half maximum of the leading edge of the histogram (the channel B, to the left of the histogram, which contains ½ as many cells as the peak channel), with the COV being 0.85 times the distance between the two channels, divided by the peak channel number;

3. creating a histogram of a Gaussian, with a standard deviation equal to the COV times the peak channel number. The value of each channel of the Gaussian histogram is $e^{-x^2/\sigma^2}$ times a constant (where x is the channel number and $\sigma$ is the standard deviation);

4. taking the fast Fourier transform of the cell distribution histogram and dividing it by the fast Fourier transform of the Gaussian 73 (shown in FIG. 4) and taking the inverse fast Fourier transform of the resulting quantity to get the deconvoluted histogram 74 of FIG. 5;

5. cutting the deconvoluting histogram into two histograms at the channel which is 8% higher than the peak channel (peak channel*1.08). The histogram 75 from channel 0 to the cutting channel is the deconvoluting $G_0$ peak of FIG. 6, with the histogram 74 from the cutting channel to channel 199 being the deconvoluting $G_2$ peak and S region, as shown in FIG. 7;

6. multiplying the fast Fourier transform of the deconvoluting $G_0$ peak by the fast Fourier transform of the Gaussian and then taking the inverse fast Fourier transform of the result to get the $G_0$ portion of the original histogram 70, as shown in FIG. 8;

7. creating a second Gaussian histogram whose standard deviation is twice that of the original Gaussian;

8. dividing the fast Fourier transform of the $G_2$ and S portion of the original histogram by the fast Fourier transform of the second Gaussian and taking the inverse fast Fourier transform of the result to get the deconvoluting $G_2$ and S shown in FIG. 9;

9. cutting the deconvoluting histogram at two times the peak channel minus 16% of the peak channel (peak channel*1.84), with the portion between channel 0 and the cutting channel being the deconvoluting S (FIG. 11) and the portion between the cutting channel and channel 199 being the deconvoluting $G_2$ (FIG. 10);

10. multiplying the fast Fourier transform of the deconvoluting $G_2$ by the fast Fourier transform of the second Gaussian, and taking the inverse fast Fourier transform of the result to obtain the $G_2$ portion of the original histogram 70 (FIG. 12).

Figure 13:
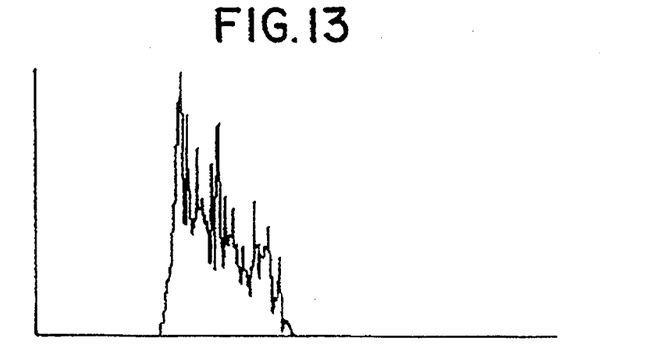

11. multiplying the fast Fourier transform of the deconvoluting S by the fast Fourier transform of the second Gaussian, and taking the inverse fast Fourier transform of the result to obtain the S portion of the original histogram 70 (FIG. 13).

Figure 14:
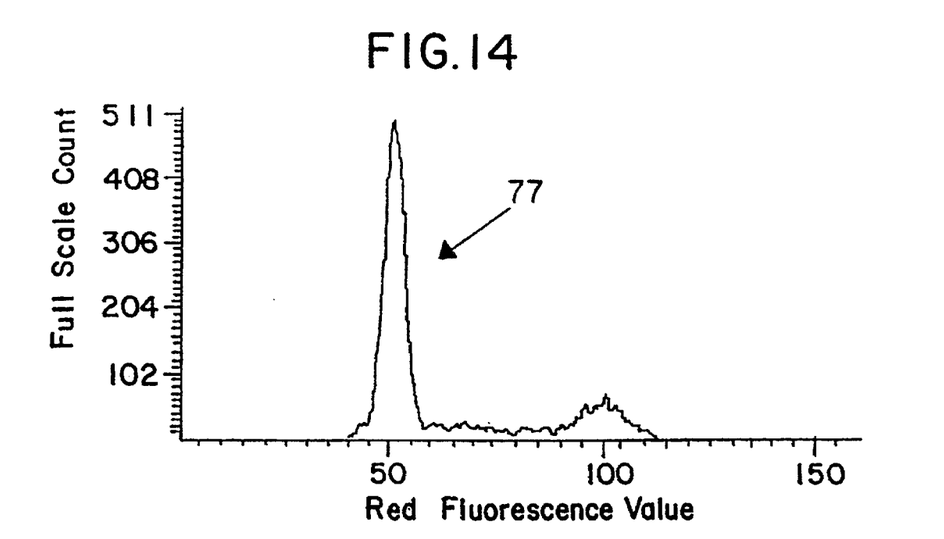
FIG. 14 is a combined histogram of the corrected $G_0$ and $G_2$ peaks and S region determined in FIGS. 4–13.
Figure 15:
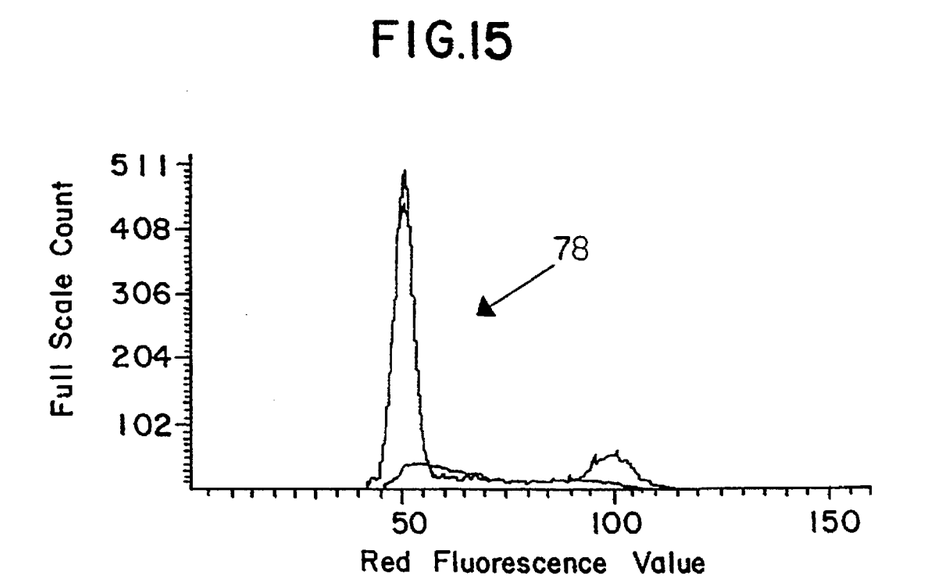
FIG. 15 is an histogram of the same sample, corrected for errors in accordance with prior art statistical methods.

A combined histogram 77 of the reconvoluted $G_0$, $G_2$ and S is prepared for the mitosis analysis, as shown in FIG. 14. An error corrected histogram 78 (FIG. 15) prepared in accordance with the procedure of the prior art significantly differs from a histogram with results which would be expected to be obtained by an actual visual inspection of the cell data of distribution in the same sample. This contrasts with the composite histogram 77 (FIG. 14) prepared in accordance with the method of the present invention, which closely tracks that of the actual expected cell data distribution. In the illustrative histograms shown, in FIG. 14 (according to the method of present invention), the populations are 71.0% in the $G_0$ phase, 17% in the $G_2$ phase and 12% in the S phase with a fitting COV of 4.8%. In FIG. 15 (according to the prior art statistical method with the same fitting COV) the populations are 60.10% in the $G_0$ phase, 14.5% in the $G_2$ phase and 25.3% in the S phase. Actual expected values, deviate by no more than about 3% from those of FIG. 14, with the prior art method providing particularly inaccurate S phase results.

Figure 16:
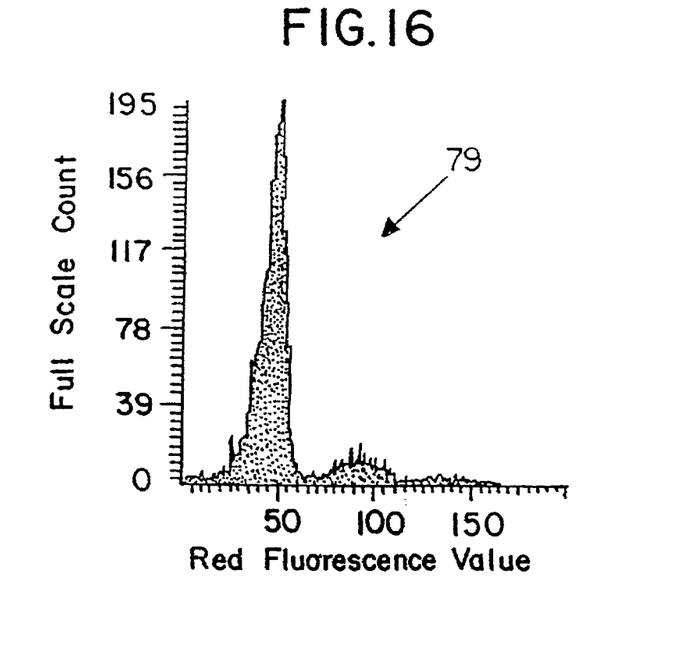
FIG. 16 is an histogram with hidden aneuploid peak.

The method of the present invention is similarly applicable to analysis of histograms of aneuploid populations. FIG. 16 is an histogram 79 with an aneuploid peak which is hidden because of a large COV. Use of the prior art commercial statistical models failed to find two peaks. However, by using the deconvolution method of the present invention (depicted in the histogram 80 of FIG. 17) the aneuploid peak 10 is clearly separated from the diploid peak 11.

Figure 17:
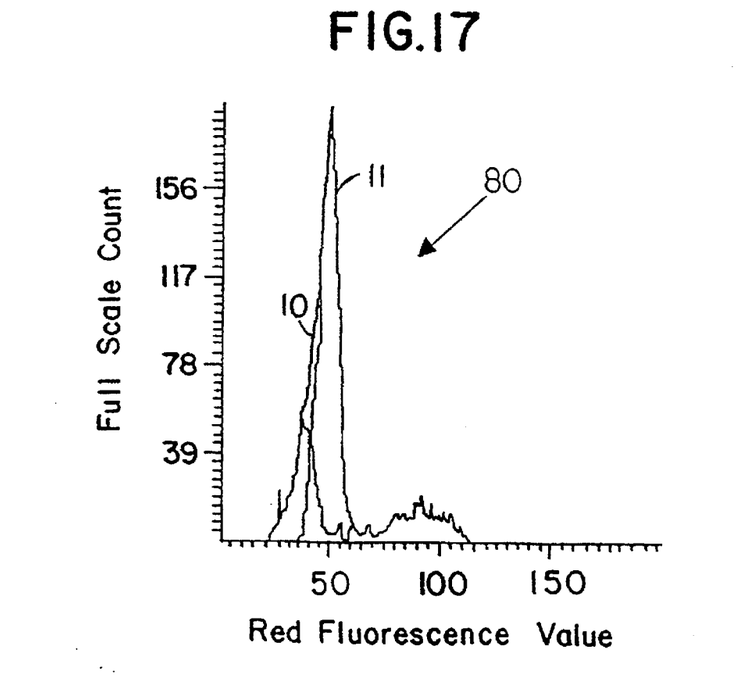
FIG. 17 is the histogram of FIG. 16, with the aneuploid and diploid peaks being visually separated.

In accordance with the present invention, in order to obtain the value of the S phase at the aneuploid peak it is initially assumed that the S phase is linear over the range of the aneuploid peak (±8%) then:

(a) the histogram is deconvoluting about the aneuploid peak;

(b) the channel counts in the histogram are averaged from 16% to 8% to the left of the peak;

(c) the channel counts in the histogram are averaged from 8% to 16% to the right of the peak;

(d) a minimum of the numbers obtained in (b) and (c) is then taken and this accounts for an aneuploid peak that is very close to either $G_0$ or $G_2$. With a peak near $G_0$, the left average includes cells in the $G_0$ and S phases. With a peak near $G_2$, the right average includes cells in the $G_2$ and S phases;

(e) the number obtained in step (d) is then substracted from all of the channel counts from 8% to the left of the peak to 8% to the right of the peak; and (f) the histogram, comprising the channel counts from 8% to the left to 8% to the right of the peak, is reconvoluted to get the aneuploid peak, which is then subtracted from the original histogram.

It is understood that the above description and drawings are exemplary of the method of the present invention and details contained therein are not to be construed as limitations on the present invention. Changes in operative steps, and components of analysis equipment and histogram parameters and the like may be made without departing from the scope of the present invention as defined in the following claims.

What is claimed is:

1. A method of preparing an histogram of a sample of biological cells, with increased accuracy, comprising the steps of:

a) staining a testing sample of biological cells with a fluorescent dye which is taken up only by DNA within the individual cells within the sample;

b) using fluorescing means to excite the taken up dye within the cells, whereby light is emitted from the individual cells, in substantial proportion to the DNA content therewithin;

c) measuring the emitted light relative to the number of cells within the testing sample and relating the measured light to DNA content within said cells;

d) preparing an histogram of relative cell populations of said testing sample having different DNA contents;

e) modeling, for each of the cell populations with differing DNA contents, the relation of the number of cells, as determined by the Fluorescence measurements, with a DNA content of a specified value, as a signal function, relative to an error function, inherent in said measurements; and d) deconvoluting the error function from the signal function with deconvolution means and correcting the histogram at each of the differing DNA contents populations to reflect substantially only the signal function.

2. The method of claim 1, wherein said deconvolution means comprises representing the histogram as:

$$H(x) = \int S(x')E(x-x')dx$$

wherein x represents the amount of DNA in a cell and the signal function S represents the number of cells with a DNA value of a particular x and E represents the error function; and wherein the signal function is deconvoluted from the error function by means of a fast Fourier transform with a relation between the histogram H(x), cell distribution S(x) and error function E($\Delta$x) being represented as:

$$S(x) = \Im^{-1}\left(\frac{\Im(H(x))}{\Im(E(\Delta x))}\right),$$

wherein the cell distribution S(x) is derived from the histogram H(x) and the error function (E$\Delta$x), by taking the inverse East Fourier transform of the quantity, the fast Fourier transform of the histogram divided by the fast Fourier transform of the error function.

3. The method of claim 2, wherein said sample comprises a cell population comprising:

a) normal cells, which are not in the process of division ($G_0$ phase) and having a base complement of DNA;

b) cells which are in the process of replicating their DNA (S phase) with varying fractional amounts of additional DNA above the base level; and c) cells which have two full complements of DNA but which have not actually divided into two cells ($G_2$ phase), and wherein said histogram comprises a measurement of relative cell populations based on their DNA content.

4. The method of claim 3, wherein the transforms are performed in a piecewise deconvolution, using a standard deviation equal to the constant coefficient of variation (COV) times the DNA value at $G_0$, wherein a $G_0$ peak that becomes apparent is subtracted out of the histogram and wherein the transforms are performed at $G_2$ and a $G_2$ peak that becomes apparent is subtracted out of the histogram.

5. The method claim 4 wherein a first heuristic is selected to create two additional initial histograms; with a first initial histogram comprising cells in the $G_0$ phase in the deconvoluted domain ($G_0$Phase(x)), and a second initial histogram comprising the cells that are not in the $G_0$ phase in the deconvoluted domain (~$G_0$Phase(x)), and wherein the ~$G_0$Phase(x) is transformed back into the undeconvoluted domain as follows:

$$H'(x) = \Im^{-1}(\Im(\sim G_0\text{Phase}(x)) * \Im(E(\Delta x)));$$ and wherein the $G_2$ phase is determined as follows:

$$S'(x) = \Im^{-1}\left(\frac{\Im(H'(x))}{\Im(E(\Delta x))}\right)$$

where E'($\Delta$x) is a Gaussian whose standard deviation is twice that of E($\Delta$x) and wherein the constant COV is assumed to be twice that of the $G_0$ population.

6. The method of claim 5 wherein it is heuristically assumed that the $G_0$ portion of the deconvoluted histogram extends 8% to either side of the $G_O$ peak.

7. The method claim 3 wherein cell sample further comprises aneuploid populations, in which some of the cells have incorrectly manufactured multiple copies of some of their DNA) and wherein an aneuploid peak rides on top of the S phase for non-aneuploid cells, and wherein the S phase is subtracted from the aneuploid peak in order to obtain the correct cell count for the aneuploid peak.

8. The method of claim 3, comprising the steps of:

a. creating an additional initial histogram having 0–199 channels from a cytometric measurement of a biological cell sample, and determining the channel, containing the most cells, to be the peak channel;

b. determining the constant coefficient of variation (COV) from the half maximum of a leading edge of the additional initial histogram, with the COV being 0.85 times the distance between the two channels, divided by the peak channel number;

c. creating a histogram of a Gaussian, with a standard deviation equal to the COV times the peak channel number, wherein the value of each channel of the Gaussian histogram is $e^{-x^2/\sigma^2}$ times a constant (where x is the channel number and $\sigma$ is the standard deviation);

d. taking the fast Fourier transform of the cell distribution histogram and dividing it by the fast Fourier transform of the Gaussian and taking the inverse fast Fourier transform of the resulting quantity to get a deconvoluted histogram;

e. cutting the deconvoluting histogram into two histograms at the channel which is 8% higher than the peak channel (peak channel*1.08), with the histogram from channel 0 to the cutting channel being a deconvoluting $G_0$ peak, and with the histogram from the cutting channel to channel 199 being a deconvoluting $G_2$ peak and S region;

f. multiplying the fast Fourier transform of the deconvoluting $G_0$ peak by the fast Fourier transform of the Gaussian and then taking the inverse fast Fourier transform of the result to get the $G_0$ portion of the original histogram;

g. creating a second Gaussian histogram whose standard deviation is twice that of the original Gaussian;

h. dividing the fast Fourier transform of the $G_2$ and S portion of the original histogram by the fast Fourier transform of the second Gaussian and taking the inverse fast Fourier transform of the result to get the deconvoluting $G_2$ and S;

i. cutting the deconvoluting histogram at two times the peak channel minus 16% of the peak channel (peak channel*1.84), with the portion between channel 0 and the cutting channel being the deconvoluting S and the portion between the cutting channel and channel 199 being the deconvoluting $G_2$;

j. multiplying the fast Fourier transform of the deconvoluting $G_2$ by the fast Fourier transform of the second Gaussian, and taking the inverse fast Fourier transform of the result to obtain the $G_2$ portion of the original histogram;

k. multiplying the fast Fourier transform of the deconvoluting S by the fast Fourier transform of the second Gaussian, and taking the inverse fast Fourier transform of the result to obtain the S portion of the original histogram l. combining the histogram of the reconvoluted $G_0$, $G_2$ and S.

9. The method of claim 7, wherein said aneuploid peak is determined and separated from the S phase in the histogram, to obtain the value of the S phase at the aneuploid peak, wherein it is initially assumed that the S phase is linear over the range of the aneuploid peak extending ±8% thereof, said method comprising the steps of:

(a) deconvoluting the histogram about the aneuploid peak;

(b) averaging the channel counts in the histogram from 16% to 8% to the left of the aneuploid peak;

(c) averaging the channel counts in the histogram from 8% to 16% to the right of the aneuploid peak;

(d) taking a minimum of the numbers obtained in (b) and (c) which accounts for an aneuploid peak that is very close to either $G_0$ or $G_2$, wherein with an aneuploid peak near $G_0$, the left average includes cells in the $G_0$ and S phases, wherein with an aneuploid peak near $G_2$, the right average includes cells in the $G_2$ and S phases;

(e) subtracting the number obtained in step (d) from all of the channel counts from 8% to the left of the aneuploid peak to 8% to the right of the aneuploid peak; and (f) reconvoluting the histogram, comprising the channel counts from 8% to the left to 8% to the right of the aneuploid peak, is reconvoluted to get a corrected aneuploid peak, which is then subtracted from the original histogram to provide the value of the S phase at the aneuploid peak.

* * * * *